United States Patent [19]

Deckert et al.

[11] Patent Number: 4,460,353
[45] Date of Patent: Jul. 17, 1984

[54] DROP CONTROLLER

[75] Inventors: Clinton L. Deckert, Poway; Jon A. Jenkins, Rancho Santa Fe; Larry L. Wilson, Poway, all of Calif.

[73] Assignee: Imed Corporation, San Diego, Calif.

[21] Appl. No.: 185,378

[22] Filed: Sep. 8, 1980

[51] Int. Cl.$^3$ ............................................. A61M 5/00
[52] U.S. Cl. .................................... 604/31; 604/34; 604/67
[58] Field of Search ....... 128/214 E, 214 F, DIG. 13, 128/214 C; 604/30-34, 65, 67

[56] References Cited

U.S. PATENT DOCUMENTS

| | | | |
|---|---|---|---|
| 3,609,379 | 9/1971 | Hildebrandt | 128/214 E X |
| 3,623,052 | 11/1971 | Spiller | 128/DIG. 13 X |
| 4,001,801 | 1/1977 | Monlet | 128/214 E X |
| 4,137,940 | 2/1979 | Faisandier | 128/214 E X |
| 4,173,224 | 11/1979 | Marx et al. | 128/DIG. 13 X |
| 4,207,871 | 6/1980 | Jenkins | 128/214 C X |
| 4,300,552 | 11/1981 | Cannon | 128/214 C X |
| 4,314,567 | 2/1982 | Cannon | 128/214 C X |

Primary Examiner—William E. Kamm
Assistant Examiner—John C. Hanley
Attorney, Agent, or Firm—Ellsworth R. Roston; Charles H. Schwartz

[57] ABSTRACT

Apparatus controls the rate of passage of fluid drops through a drip controller in accordance with a preset rate. When the rate of passage of the fluid drops is less than the preset rate, a stepper motor is incrementally operated at progressive instants of time to open the drip chamber until the measured rate is equal to the preset rate. When the rate of passage of the fluid drops is greater than the preset rate, the stepper motor is operated instantaneously to close the passage through a number of increments corresponding to the difference in the measured and preset rates.

An alarm is energized when the stepper motor is positioned to provide for a maximum flow of fluid and the rate is still below the preset rate. An alarm is also energized when the passage is closed and the preset rate indicates a desired flow of fluid.

An emergency motor is also provided to control the opening in the passage. Before the operation of the apparatus is instituted, the stepper motor is operated to close the drip chamber. The emergency motor is then operated to open the drip chamber and thereafter close the drip chamber. The emergency motor may thereafter be operated to close the passage when the drop controller fails to meet certain standards.

34 Claims, 9 Drawing Figures

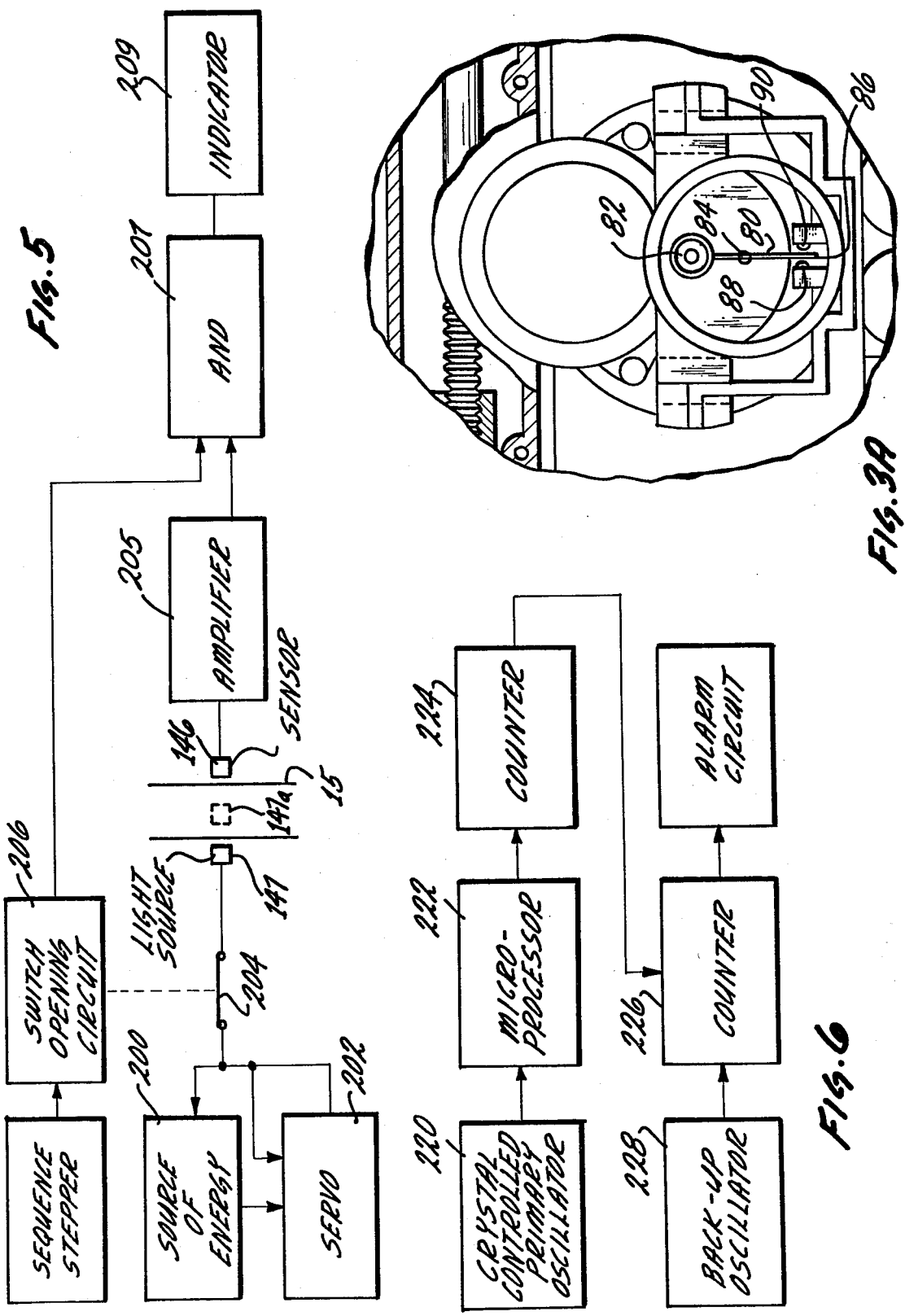

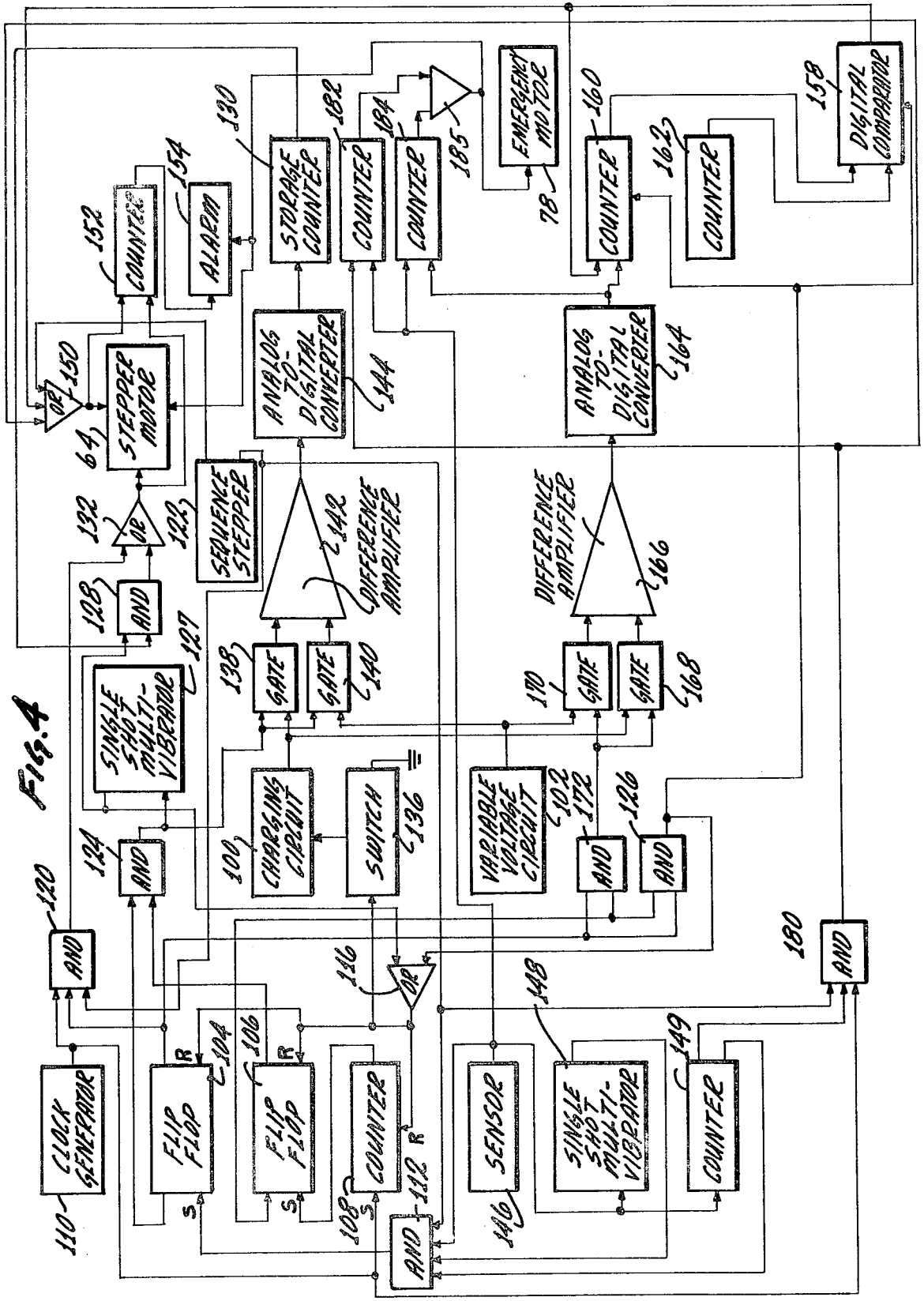

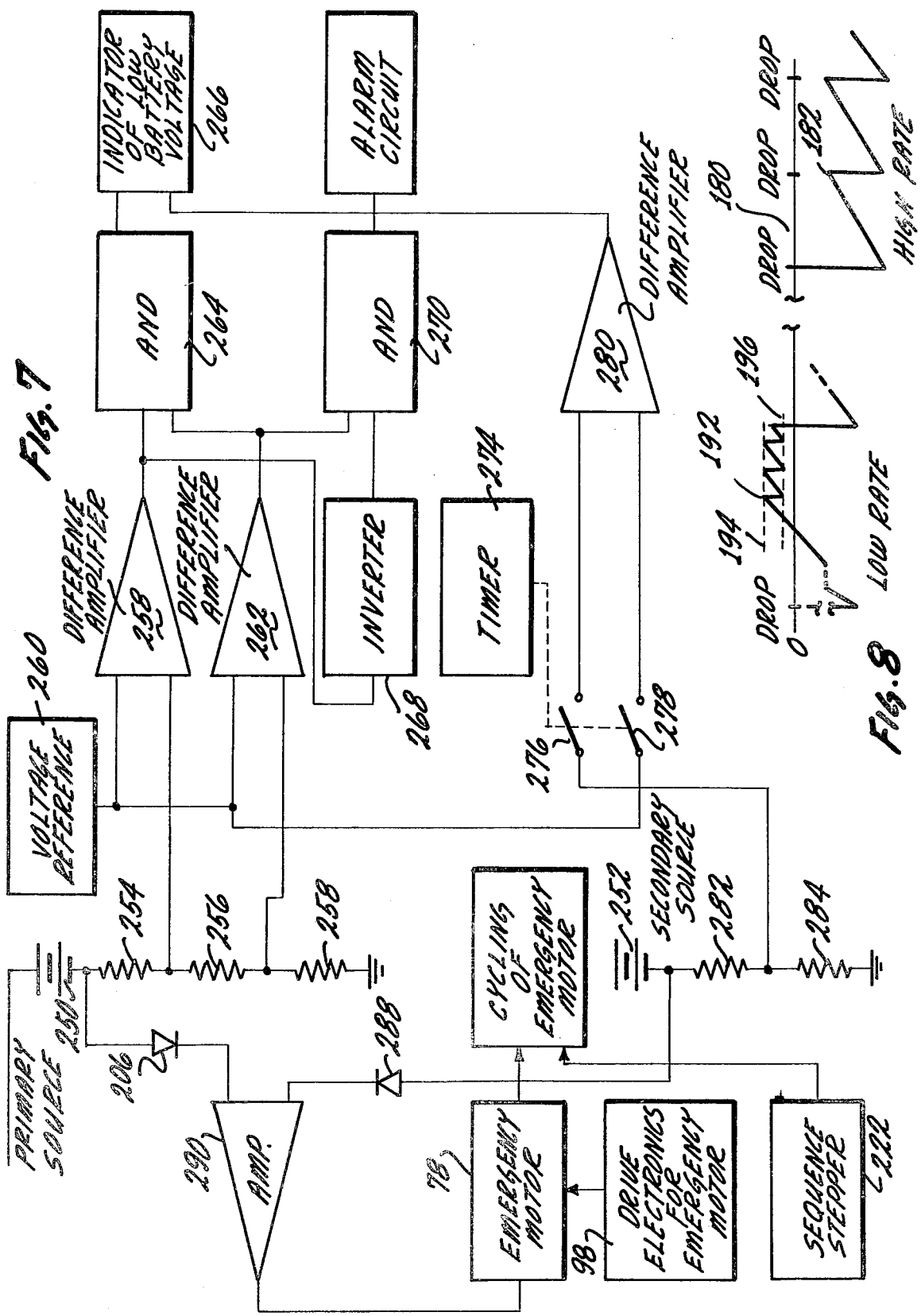

DROP CONTROLLER

BACKGROUND OF THE INVENTION

This invention relates to apparatus for controlling the flow of fluid drops through a drip chamber so that the rate corresponds to a preset rate. The invention particularly relates to a fail-safe system for providing for a flow of fluid drops on a gravitational basis through the drip chamber at a preset rate. The invention is especially adapted to be used in controlling the flow of intravenous fluid on a gravitational basis through a drip chamber from a source to a patient.

As the practice of medicine becomes progressively complex and refined, the equipment and techniques to provide care for a patient have become increasingly sensitive in order to assure that the patient receives optimum care. For example, after an operation has been performed on a patient and the patient is in the recuperative state, intravenous fluid has often been introduced to the patient. The rate of introduction of intravenous fluid to the patient is dependent upon a number of different factors including the weight, age, sex and physical state of the patient. As the patient recovers from his illness, the rate of introduction of the intravenous fluid to the patient is preferably adjusted to assure that the patient receives an optimum benefit from the fluid.

Drop controllers have been used in the prior art to control the rates at which drops of fluid have been passed to a patient. Such drop controllers have provided for the passage of drops of the fluid on a gravitational basis to the patient. Such drop controllers have been relatively crude. They have provided for the clamping of a conduit to control the rate at which the fluid is passed to the patient. Such clamping has been relatively unreliable in controlling the rate of fluid flow. Furthermore, the drop controllers of the prior art have not provided fail-safe features so that patients have been injured when the controllers have failed to operate properly.

Copending application Ser. No. 938,910, now abandoned has been filed by Raymond E. Cannon on Sept. 1, 1978, for "Apparatus for Controlling the Flow of Intravenous Fluid to a Patient" and has been assigned of record to the assignee of record of this application. This copending application discloses and claims a disposable cassette which passes fluid at a controlled rate on a gravitational basis to a patient. The cassette can be used by itself to provide an accurate control over the passage of fluid at a rate preselected in accordance with the manual operation of a knob included in the cassette. The cassette can also be disposed in electronic equipment to provide for a passage of fluid through the cassette in accordance with the operation of settings provided on the face of the controller. The electronic settings have precedence over any manual positioning of the knob. In this way, the cassette can be controlled manually or the manual control can be superseded when the cassette is disposed in electronic equipment. Furthermore, each cassette can be discarded after use by a patient and a new cassette can be provided for the next patient without any need to sterilize the drop controller between uses.

Application Ser. No. 078,573 now U.S. Pat. No. 4,314,567 has also been filed by Raymond E. Cannon on Sept. 24, 1979, for a "Drop Controller" and has been assigned of record to the assignee of record of this application. The drop controller disclosed and claimed in application Ser. No. 078,573 provides for a fixed, but easily releasable, coupling between the cassette and the drop controller. The drop controller also includes apparatus for operating upon a passage in the cassette to control the rate at which fluid is passed through the passage. The drop controller further includes apparatus for closing the passage when the apparatus controlling the rate of passage of the fluid drops through the passage is not functioning properly. Apparatus is also included for testing the operation of the drop controller before every use of the drop controller by closing and then opening the passage.

This invention discloses and claims electronic equipment for use with the cassette disclosed and claimed in application Ser. No. 938,910 and with the apparatus disclosed and claimed in application Ser. No. 078,573 in providing for a passage of fluid through a passage at a precise rate dependent upon a rate preset in the electronic equipment. The electronic equipment is further advantageous in providing certain tests on the cassette and the drop controller before the passage of fluid through the drip chamber at the controlled rate is initiated. In this way, proper operation of the drop controller is assured. The electronic equipment is also advantageous in providing fail-safe operation of the drop controller and in discontinuing the operation of the drop controller or producing alarms when the drop controller is not operating properly.

The electronic equipment operates to control the rate of passage of the fluid drops through a drop controller in accordance with a rate preset in the electronic equipment. When the rate of passage of the fluid drops is less than the preset rate, a stepper motor is incrementally operated at progressive instants of time to open the passage until the measured rate is equal to the preset rate. When the rate of passage of the fluid drops is greater than the preset rate, the stepper motor is operated instantaneously to close the passage through a number of increments corresponding to the difference between the measured and preset rates.

An alarm is energized under certain conditions. For example, an alarm is energized when the stepper motor is positioned to provide for a maximum flow of fluid and the rate is still below the preset rate. An alarm is also energized when the passage is closed and the preset rate indicates a desired flow of fluid.

An emergency motor is also provided to control the opening in the passage. Before the operation of the drop controller is instituted, the stepper motor is operated to close the drip chamber. The emergency motor is then operated to open the drip chamber and thereafter close the drip chamber. The emergency motor may thereafter be operated to close the passage when the drop controller fails to meet certain standards.

The passage of the drops through the drip chamber is sensed by introducing light from a source to the chamber and detecting the light passing from the chamber. The current passing to the light source is servoed to maintain the current at a substantially constant value. This facilitates the detection by the sensor of the fluid drops passing through the sensor. The current to the light source may be instantaneously reduced and the signal at the sensor may be detected at such instant to determine if the sensor is operative.

Primary and secondary sources of energy may be provided in the electronic equipment. The primary and secondary sources of energy may be tested to determine if they are at sufficient strength to operate the control apparatus. The primary and secondary sources are connected to provide for an operation of either one of the sources when an emergency condition exists.

A first oscillator produces an operation of a microprocessor at a particular clock frequency. The microprocessor processes data to maintain the rate of passage of the fluid drops through the drip chamber at the preset rate. When the clock frequency of the microprocessor falls below a particular value, an alarm is energized.

After tests such as those described above have been made, the operation of the control apparatus may be initiated. The stepper motor may then be operated to open the drip chamber until the passage of the first drop through the drip chamber is detected. The stepper motor may thereafter be controlled as described above to maintain the rate of passage of the fluid drops through the drip chamber at the preset rate.

IN THE DRAWINGS

FIG. 3A is an enlarged fragmentary plan view, in section of the controller;

FIG. 4 is a schematic block diagram of electronic equipment included in the drop controller for regulating the rate at which drops of fluid are passed through a drip chamber to maintain such rate in accordance with a preset rate;

FIG. 5 is a schematic block diagram of electronic equipment included in the drop controller for regulating the operation of transducers for sensing the passage of the fluid drops through the drip chamber and for testing for the sensing of the passage of such fluid drops through the drip chamber;

FIG. 6 is a schematic block diagram of electronic equipment included in the drop controller for testing for the proper operation of a microprocessor which operates upon the sensed data to maintain the passage of the fluid drops through the drip chamber at a preset rate;

FIG. 7 is a schematic block diagram of electronic equipment included in the drop controller for testing the sources of energy to the electronic equipment and for obtaining a closure of the drip chamber under certain conditions of inoperability; and FIG. 8 schematically illustrates wave forms showing voltages produced when the actual rate of passage of the fluid drops is less than a preset rate.

DETAILED DESCRIPTION OF THE INVENTION

Figure 1:
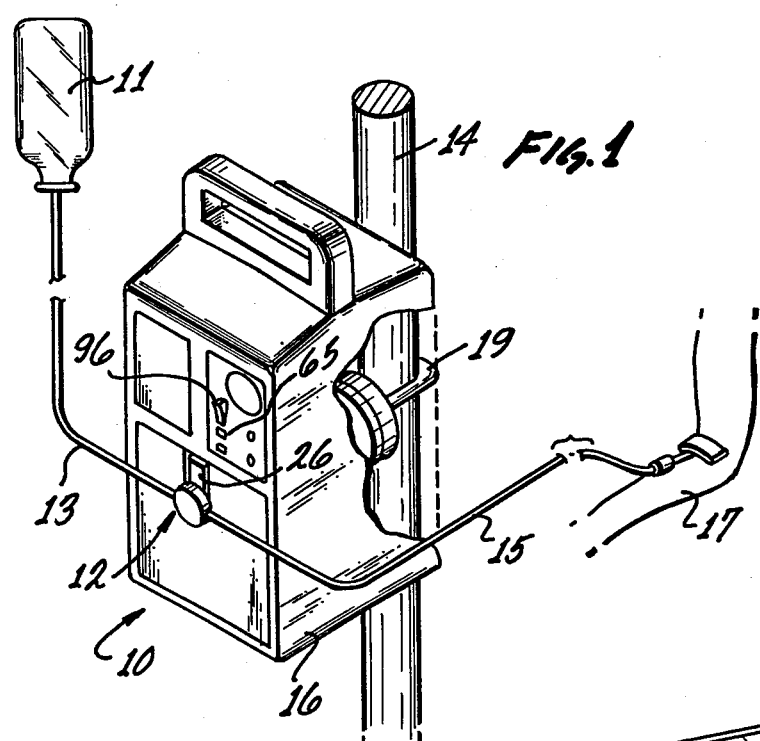
FIG. 1 is a perspective view, partially broken away, of a drop controller forming one embodiment of the invention and of a cassette adapted to be used with such drop controller to control the rate at which drops of fluid are passed on a gravitational basis to a patient.
Figure 2:
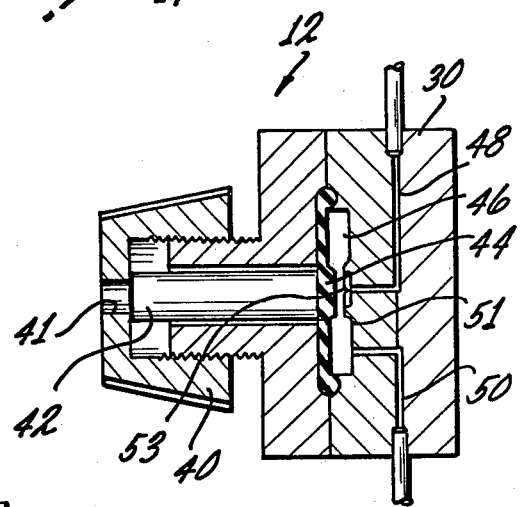
FIG. 2 is an enlarged sectional view of the cassette shown in FIG. 1.

In the embodiment of the inventions shown in the drawings, a drop controller generally indicated at 10 is provided to produce a flow of fluid at a precise rate. The drop controller may be adapted to operate in conjunction with a cassette, generally indicated at 12, to control the rate at which fluid, such as intravenous fluid, flows to a patient. The flow of fluid is provided from a source 11 through an input conduit 13, the cassette 12 and a drip chamber 15 to a patient 17. The drop controller 10 and the cassette 12 may be constructed as described and shown in copending applications Serial Nos. 938,910 and 078,573 assigned of record to the assignee of record of this application. The drop controller is adapted to be supported on a pole 14 as by an adjustable clamp 19.

Figure 3:
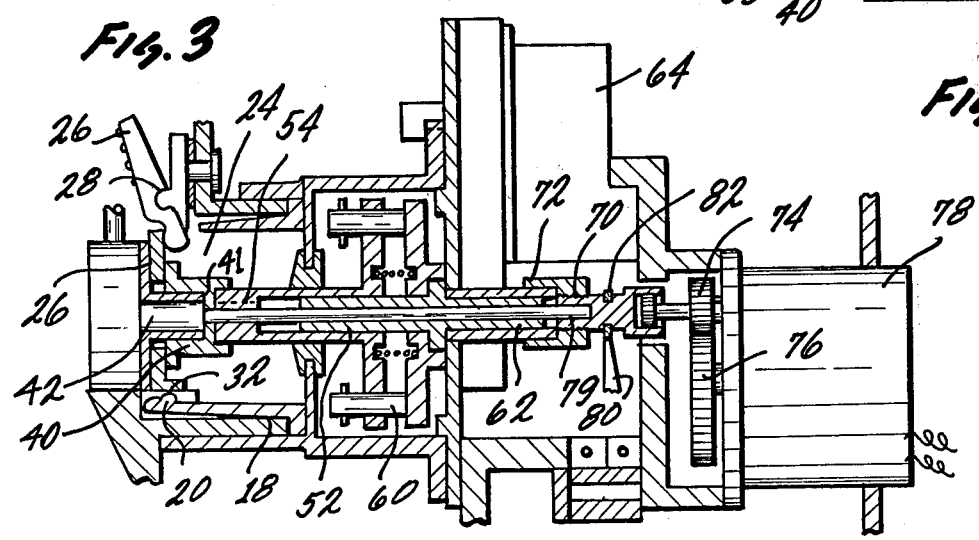
FIG. 3 is an enlarged sectional view of the cassette shown in FIGS. 1 and 2 and of certain mechanical features included in the drop controller shown in FIG. 1.

The drop controller 10 includes a housing 16. The housing 16 includes a plurality of spring fingers 18 having detents 20 at or near their spring ends. The spring fingers are disposed in an annular configuration to define a socket 24. A lever 26 is pivotably supported at an intermediate position by a button 28 on the housing so as to define a relatively short lever arm below the button 28 and a relatively long lever arm above the button. The lower lever arm is disposed in the socket in one pivotable position, as shown in FIGS. 1 and 3.

The cassette 12 is provided with a housing 30 having detents 32 for cooperating with the detents 20 to retain the cassette in fixed position when the cassette is inserted into the socket. The cassette 12 is also provided with a wall 34 against which the lower arm of the lever 26 is disposed when the cassette is retained by the spring fingers 18 within the socket 24. When it is desired to remove the cassette 12 from the socket 24, the arm of the lever 26 is pressed toward the right in FIGS. 1 and 3. This produces a multiplication of force on the lower arm of the lever 26 to remove the cassette from the socket.

The cassette 12 may be provided with a rotatable knob 40 which is disposed within the controller housing 16 when the cassette is retained within the socket 24. The knob is open at a central position as indicated at 41. The knob 40 presses against a pusher rod 42 to control the positioning of a resilient diaphram 44 in a passage 46. The passage 46 communicates with an inlet conduit 48 and an outlet conduit 50. A button 51 is disposed in a closed loop at a position enveloping one of the inlet conduit 48 and the outlet conduit and a notch 53 is cut in the button. The notch 53 is closed by the diaphragm 44 through a distance dependent upon the rotational setting of the knob 40. In this way, the knob 40 acts on the pusher rod 42 to control the size of the opening defined by the passage, thereby controlling the rate at which drops of fluid flow through the passage 46.

A pusher member 52 is disposed in the controller 10 and is coupled to the knob 40 by a detent arrangement 54, preferably spring-biased, when the cassette 12 is properly positioned in the socket 24. The pusher member is in turn coupled through a yoke 60 to a hollow drive member 62 in a stepper motor 64. The motor 64 is stepped through a number of precise increments dependent upon the selection of digital settings 65 on the front of the housing 16. When the motor 64 is incrementally operated, it rotatably adjusts the positioning of the pusher member 52 and the member 52 in turn rotatably drives the knob 40 to constrain the diaphragm 44 and thereby adjust the size of the opening in the passage 46. The positioning of the pusher member 52 has precedence, in controlling the size of the opening in the passage 46, over any setting made manually in the knob 40 before the insertion of the cassette into the socket.

A threaded extension 70 is rotatably disposed within an internally threaded collar 72 having a stationary disposition. The threaded extension 70 is driven by a gear 74 which is in mesh with a gear 76 driven by a suitable motor 78 such as a D.C. motor. The threaded extension in turn drives a rod 79 which extends through the opening 41 in the knob 40 and presses against the pusher rod 42.

A yoke 80 is suitably mounted on the threaded extension 70 as by a sleeve 82. The yoke 80 is pivotally mounted as at 84 at an intermediate position along its length. The yoke 80 is provided at its outer length with a flag 86 which is movable at one extreme position between a light source 88 and a photocell 90 and at an opposite extreme position between a light source corresponding to the light source 88 and a photocell corresponding to the photocell 90.

The photocell 90 and the corresponding photocell and the motor 78 are included schematically in electrical circuitry 98 shown in block form in FIG. 7 and designated as "Drive Electronics for Electric Motor". Since the electrical circuitry is shown in block form and the motor 78 and the photocells are included in this electrical circuitry, the motor 78 and the photocells are not specifically shown in FIG. 7. In accordance with the operation of this circuitry, the motor 78 is driven in opposite directions after the cassette 12 has been properly inserted into the controller 10. The motor 78 is driven in this manner when the operation of the controller is initiated by the closure of a switch 96 on the front of the housing 16 and the digital settings 66 have been set to a particular value. The operation of the motor 78 causes the rod 79 to be pressed against the pusher rod 42 and the diaphragm 44 to be constrained in a direction for initially closing the passage 46 and for subsequently opening the passage. This insures that the passage 46 can be closed by the motor 78 if the controller 10 becomes inoperative in any way. In this way, a patient cannot be subjected to injury as a result of an improper operation or an inoperation of the controller 10.

FIG. 4 schematically illustrates a circuit diagram in block form of certain features included in the drop controller described above. The circuit diagram of FIG. 4 includes a charging circuit 100 which may be constructed in a conventional manner to charge a capacitor so that the capacitor provides a ramp voltage. The circuit of FIG. 4 also includes a variable voltage source 102 which may be set at a voltage dependent upon the selection of the digital settings 66 on the front panel of the drop controller.

The circuit of FIG. 4 also includes a pair or flip-flops 104 and 106 each having two stable states of operation respectively designated as "set" and "reset". The set input terminal of the flip-flop 104 receives input signals from an AND network 112. The reset input terminal of the flip-flop 104 is connected to the output terminal of an OR network 116. The set input terminal of the flip-flop 106 is connected to the output of a counter 108 and the reset input terminal of the flip-flop 106 is connected to the output terminal of the OR network 116. The counter 108 counts the signals from a clock generator 110 and produces a signal for triggering the flip-flop 106 to the set state when the count reaches a particular value. The counter 108 is reset to zero by a signal from the OR network 116.

The reset output terminal of the flip-flop 104 is connected to an input terminal of an AND network 120 having other input terminals respectively connected to a sequence stepper 122 and the clock generator 110. The set output terminal of the flip-flop 104 has a connection to an input terminal of an AND network 124, another input terminal of which receives the voltage on the reset output terminal of the flip-flop 106. Connections are made from the set output terminals of the flip-flops 104 and 106 to an AND network 126.

The output signals from the AND network 124 are introduced to the set input terminal of a single shot multivibrator 127 having its set output terminal connected to an input terminal of an AND network 128. Another input terminal of the AND network 128 is connected to an output terminal of a storage counter 130. The output signals from the AND network 128 pass through an OR network 132 to the stepper motor 64 to produce an operation of the motor in a direction for closing the passage 46. Signals for closing the passage also are introduced through the OR network 132 from the AND network 120.

The signals from the OR network 116 are introduced to a switch 136 having one terminal grounded. When the switch 136 is operated, it connects the charging circuit 100 to ground to discharge the capacitor included in the charging circuit 100. The output from the charging circuit 100 is connected to input terminals of a pair of gates 138 and 140. The gate 138 has its second input terminal connected to the output of the AND network 124. The second input terminal of the gate 140 is connected to the variable voltage circuit 102. The outputs of the gates 138 and 140 are applied to input terminals of a difference amplifier 142, the output from which passes to an analog-to-digital converter 144. A connection is made from the output of the converter 144 to an input terminal of the storage counter 130.

An output from the sequence stepper 122 is also introduced to an input terminal of the AND network 112 having input terminals connected to a sensor 146 and the reset output terminal of a single shot multivibrator 148. The output from the sensor 146 is also introduced to the set input terminal of the single shot multivibrator 148 and a counter 149. The sensor 146 is associated with a light source 147 to sense the light passing through the conduit 15. Instead of using a single source 147, a pair of light sources 147 and 147a may be disposed at spaced positions around the periphery of the conduit 15. The light source 147a is shown in broken lines in FIG. 5. The light sources 147 and 147a direct light to the photocell 146. By providing more than one light source, such adverse effects as clouding of the conduit 15 by vapor from drops passing through the conduit are minimized.

An output terminal of the sequence stepper 122 is connected to an input terminal of an OR network 150 having another input terminal connected to the output terminal of a digital comparator 158. The signals passing through the OR network 150 operate the stepper motor 64 in a direction to close the passage 46. The signals passing through the OR network 150 are also introduced to a counter 152 to provide a count in one direction and the signals passing through the OR network 132 are introduced to the counter to provide a count in an opposite direction. The output of the counter 152 is introduced to an alarm 154 to energize the alarm when the count in the counter 152 has a particular value.

The digital comparator 158 receives the output from a pair of counters 160 and 162 and also receives the output from the AND network 126. The counter 162 is preset to a particular value. The counter 160 has input terminals connected to the digital comparator 158 and to an analog-to-digital converter 164. The converter 164 converts to a digital representation analog signals from a difference amplifier 166.

Input terminals of the difference amplifier 166 are connected to the output terminals of gates 168 and 170. First input terminals of the gates 168 and 170 are respectively connected to the charging circuits 100 and the variable voltage circuit 102. Second input terminals of the gates 168 and 170 are connected to an AND network 172, the input terminals of which receive the voltages on the reset output terminal of the flip-flop 104 and the set output terminal of the flip-flop 106.

An AND network 180 has input terminals connected to the sequence stepper 122, a clock generator 110 and the counter 149. The output terminal of the AND network 180 is connected to the counter 160 and the digital comparator 158. The AND network 180 also has its output terminal connected to input terminal of counters 182 and 184, second input terminals of the counters 182 and 184 being connected to the sensor 146. The counters 182 and 184 in turn control the operation of the emergency motor 78 by introducing signals to an OR network 185 which is connected to the emergency motor 78. The signals from the OR network 185 are also introduced to the stepper motor 64 to stop the motor.

The sequence stepper 122 provides signals representing different steps in a sequence of operations. As will be explained subsequently in detail, some of these steps involve tests which are made on the drop controller before the passage of fluid drops through the passage 46 is initiated. After such tests have been made, the sequence stepper 122 is stepped to a position to provide for an opening of the passage 46 so that the passage of the fluid drops through the drip chamber 15 can be initiated.

To institute an opening of the passage 46, clock signals from the generator 110 pass through the "and" network 180 which is open at this time because the count in the counter 149 is zero. The clock signals passing through the AND network 180 are introduced through the OR network 150 to the stepper motor 150 to operate the motor in a direction for opening the passage 46. The passage 46 continues to open until the passage of a fluid drop.

When the passage 46 has been opened sufficiently, a fluid drop passes through the passage 46. This fluid drop produces a signal in the sensor 146. The signal from the sensor 146 operates the counter 149 to set the counter to a value of "1". This opens the AND gate 180 and causes the stepper motor 64 to stop.

The next fluid drop in the drip chamber causes the sensor 146 to produce a signal which is introduced to the AND network 112. The AND network 112 has been previously activated by the signal from the sequence stepper 122. The signal from the sensor 146 is accordingly able to pass through the AND network 112 because the single shot multivibrator 148 is in its reset state and because the counter 149 provides a count indicating that a fluid drop has previously passed through the drip chamber.

The signal from the sensor 146 is also introduced to the set input terminal of the multivibrator 148 to trigger the multivibrator to the set state. However, the multivibrator 148 is provided with a slight time delay to insure that it will be triggered to the set state only after the signal from the sensor 146 is able to pass through the AND network 112. When the single shot multivibrator 148 is triggered to the set state, signals are not able to pass through the AND network 112 because of the production of a relatively low voltage on the reset output terminal of the multivibrator. In this way, the AND network 112 is inhibited for a time period corresponding to the time that splash-ups may occur in the drip chamber from the passage of a fluid drop through the drip chamber.

The signal passing through the AND network 112 triggers the flip-flop 104 to the reset state. This causes a relatively high voltage to be introduced from the set output terminal of the flip-flop 104 to the AND network 124. If the flip-flop 106 is still in its reset state, a signal passes through the AND network 124. This signal indicates that the fluid drops are passing through the passage 46 at a rate greater than the preset rate selected by the operation of the settings 66.

The passage of the fluid drops through the drip chamber at a rate greater than the particular rate may be seen from the fact that, at the time the flip-flop 104 becomes set, the voltage 182 (FIG. 8) in the charging circuit 100 is less than the voltage 180 preset in the variable voltage circuit. The difference in the voltages 180 and 182 represents the difference in the preset time between the passage of successive fluid drops and the actual time between the passage of successive fluid drops.

The signal passing through AND network 124 activates the gates 138 and 140 so that the voltages on the charging circuit 100 and the variable voltage circuit 102 respectively pass through the gates 138 and 140 to the difference amplifier 142. The voltage in the circuit 102 is selected by the operation of the settings 65. This voltage is indicated at 180 in FIG. 8. The voltage on the charging circuit 100 is dependent upon the period of time between each successive pair of fluid drops passing through the passage 46.

The difference amplifier 142 produces an output voltage representative of the difference in the voltages from the charging circuit 100 and the variable voltage circuit 102. This voltage is converted by the converter 144 into a digital representation and the digital representation is introduced to the storage counter 130. The count in the counter 130 is introduced to the AND network 128, which is activated for a particular period of time by the triggering of the single shot multivibrator 127 to the set state.

During the time that the multivibrator 127 is in the set state, the count from the counter 130 causes the stepper motor 64 to be stepped through a number of increments corresponding to the count in the counter 130. As the stepper motor is stepped through each increment, the count in the counter is decreased by an increment. In this way, the stepper motor 64 is stepped through a number of increments corresponding to the difference in voltages between the charging circuit and the variable voltage circuit 102.

When the single shot multivibrator 126 is triggered to the set state, a signal passes through the OR network 116 and triggers the flip-flop 104 to the reset state. The signal also passes to the reset input terminal of the flip-flop 106 to insure that this flip-flop is in the reset state. The signal also passes to the switch 136 and closes the switch to ground so that the charging circuit 100 becomes discharged.

It may be that the rate of the fluid drops passing through the passage 46 is less than the preset rate represented by the selection of the digital settings 65. Under such circumstances, the counter 108 reaches a full count of clock signals. The value of this full count is dependent upon the selection of the digital settings 65. When the counter 108 reaches a full count, it introduces a signal to the reset input terminal of the flip-flop 106 to trigger the flip-flop to the set state. This causes a high voltage to be introduced from the set output terminal of the flip-flop 106 to the gate 172. At such time, the flip-flop 104 is still in the reset state because a fluid drop has not been sensed by the sensor 146.

When the flip-flop 104 is in the reset state and the flip-flop 106 is in the set state, a signal passes through the AND gate 172 to the gates 168 and 170 to energize the gates. The gate 170 then passes the voltage from the variable voltage circuit 102 and the gate 168 passes the voltage on the charging circuit 100. The difference between the voltages in the charging circuit 100 and the variable voltage circuit 102 is determined by the amplifier 166 and this difference is converted to a digital form by the converter 164. The digital indications from the converter 164 are introduced to a counter 160.

As will be seen in FIG. 8, the voltage from the charging circuit 100 increases above the voltage 180 from the circuit 102 as the time between the passage of successive fluid drops through the passage 46 increases above the time represented by the counter 108. This is illustrated at 192 in FIG. 8. When the difference in the voltages in the charging circuit 100 and the variable voltage circuit 102 reach a particular value 194, the count representative of this difference in the counter 160 equals a count preset in the counter 162. This causes a signal to be produced by the digital comparator 158. This signal passes through the OR network 150 to the stepper motor to step the motor through one increment in a direction for opening the passage 146.

The signal from the digital comparator 158 is also introduced to the counter 160 to reduce the count in the counter 160 by a particular number of increments. This is indicated at 196 in FIG. 8. If a fluid drop still fails to pass through the passage 46 for a particular period of time, the count in the counter 160 again increases to the count preset in the counter 162. The digital comparator 158 again produces a signal which causes the stepper motor 64 to step through an increment in a direction for opening the passage 46. At the same time, the count in the counter 160 is decreased through the particular number of increments. In this way, the stepper motor 64 is stepped periodically to open the passage 46 through individual increments at progressive instants of time until a fluid drop passes through the passage 46.

As previously described, the AND gate 180 becomes opened when the stepper motor 64 starts to operate incrementally in a direction to open the passage 46. At such time, the clock signals from the generator 110 pass through the AND gate 180 to the counter 182, which counts the clock signals. If a fluid drop does not flow through the drip chamber after a particular number of counts, the counter 182 introduces a signal to the stepper motor 64 to stop the stepper motor. At the same time, the counter 182 introduces a signal through the OR network 185 to the emergency motor 78. The emergency motor 78 then operates in a direction to close the passage 46.

The emergency motor 78 also operates to close the drip chamber when it receives a signal from the counter 184. The counter 184 counts the signals introduced from the comparator 158 to the stepper motor 64 to open the passage 46 incrementally. When the count in the counter 184 reaches a particular value without the passage of a drop through the drip chamber, the operation of the stepper motor 64 is interrupted and the emergency motor 78 is operated to close the drip chamber.

There may be a time when the drip chamber is fully open and the rate of passage of fluid drops through the drip chamber may be still low. Under such circumstances, a particular count is provided in the counter 152 to indicate the operation of the stepper motor to the fully open position of the drip chamber. This particular count causes an alarm 154 to be operated. The particular count is able to be produced because the counter 152 counts in opposite directions in accordance with the introduction of signals from the OR networks 132 and 150. The signals from the OR network 185 may also be introduced to the alarm 154 to operate the alarm.

Although circuitry for controlling the operation of the stepper motor 64 and the emergency motor 78 is shown schematically in FIG. 4 and is described in detail above, it will be appreciated that other circuitry may be provided to accomplish the same or similar functions. For example, a microprocessor may be programmed to accomplish the same or similar functions as described above. Such a microprocessor may actually be preferred to the circuitry of FIG. 4 because of its relative simplicity. It is believed that a person skilled in the art will be able to program the microprocessor on the basis of the above discussion and the circuitry shown in FIG. 4.

FIG. 5 schematically illustrates circuitry for maintaining a proper operation of the light source 88 and the sensor 146 and for testing for this proper operation. The circuitry shown in FIG. 5 includes a source 200 of energy. A servo 202 is connected in a closed loop with the source of energy to maintain the energy from the source at a substantially constant value. The constant energy is then introduced through a normally closed switch 204 to the light source 88. In this way, the energy introduced to the source 88 is maintained substantially constant so that the only change in the intensity of the signal produced in the sensor 146 results from the flow of a fluid drop through the passage 46.

The opening of the switch 204 is controlled by a switch opening circuit 206, the operation of which is controlled by the sequence stepper 122. When the switch 204 is opened by the circuit 206, the introduction of energy to the source 88 is interrupted. This causes a signal to be produced by the sensor 146 corresponding to the signal which is produced when a fluid drop passes through the passage 46. This signal is amplified by a stage 205 and is introduced to an input terminal of an AND network 207, another input terminal of which is connected to the circuit 206. The output of the AND network 207 is connected to an indicator 209.

When the switch 204 is opened, a signal is produced by the sensor 146 to represent the passage of a fluid drop through the passage 46 and is introduced to the AND network 207. This signal passes through the AND network 207 because the AND network is opened by the operation of the circuit 206. The signal then operates the indicator 209 to indicate that the sensor 146 is operative. If the sensor 146 is not operative, the indicator 209 will produce a signal to show this. This signal may be introduced to the alarm 154 in FIG. 4 to operate the alarm.

As previously indicated, the circuitry shown in FIG. 4 may be included in a microprocessor. Whether the circuitry is included in a microprocessor or is constructed as shown in FIG. 4, the rate for processing the information may be controlled by an oscillator such as a crystal controlled primary oscillator 220 shown in FIG. 6. The signals from the oscillator 220 are shown in FIG.

6 as controlling the processing of data in a microprocessor 222 which may be considered to represent the circuitry shown in FIGS. 4 and 5 and even FIGS. 6 and 7. The signals from the microprocessor are in turn introduced to a counter 224 which counts the binary bits of information progressively being processed by the microprocessor 222. The output from the counter 224 is introduced to a counter 226 which counts digital signals produced by a backup oscillator 228. The backup oscillator operates at a particular frequency less than the frequency normally produced by the oscillator 220. An output terminal of the counter 226 is connected to the alarm 154 also shown in FIG. 4.

The signals from the oscillator 220 control the rate at which the digital information is processed by the microprocessor 222. Signals produced by the microprocessor 222 to represent successive bits are introduced to the counter 224 to provide a count in the counter. When the count in the counter 224 reaches a particular value, it introduces a signal to the counter 226 to reset the counter provided that the count in the counter 226 has not reached the particular value. At the same time, the count in the counter 224 become reset.

It may occur that the microprocessor 222 becomes inoperative so that the count in the counter 224 is not produced at the desired rate. Under such circumstances, the count in the counter 226 may reach the particular value before the counter 224 reaches such particular count. The counter 226 then introduces a signal to the alarm 154 to operate the alarm. The alarm is operated because the improper operation of the microprocessor 222 prevents the fluid drops from passing through the passage 46 at the preset rate.

FIG. 7 schematically illustrates circuitry for testing primary and backup sources of voltage to insure their proper strength and for introducing voltages from the batteries to operate the emergency motor 78. The circuitry shown in FIG. 6 includes a primary source 250 of energy and a secondary source 252. The voltage from the primary source 250 is connected to a reference potential such as ground through a voltage dividing network including resistors 254, 256 and 258 in series. The terminal common to the resistors 254 and 256 is connected to an input terminal of a difference amplifier 258 having a second input terminal connected to a voltage reference 260. The voltage reference 260 and the terminal common to the resistors 256 and 258 are connected to a difference amplifier 262. The outputs of the difference amplifiers 258 and 262 are introduced to input terminals of an AND network 264 having its output terminal connected to an indicator 266 of low battery voltage.

The voltage on the output terminal of the amplifier 258 is inverted in a stage 268, and the inverted voltage is introduced to an input terminal of an AND network 270 having a second input terminal connected to the difference amplifier 262. The output of the AND network 270 is introduced to the alarm 152.

A timer 274 controls the closing of switches 276 and 278 on a cyclic basis. One terminal of the switch 276 is connected to the voltage reference 260 and the other terminal is connected to an input terminal of a difference amplifier 280. One terminal of the switch 278 is connected to a terminal common to a pair of series resistors 282 and 284 which are in series between the secondary source 252 and the reference such as ground. The output from the difference amplifier 280 is introduced to the indicator 266 of low battery voltage.

The output voltages from the primary source 250 and the secondary source 252 are introduced through diodes 286 and 288 to an amplifier 290. The output from the amplifier 290 operates the emergency motor 78.

The voltage from the primary source 250 is divided by the resistors 254, 256 and 258. Even with this division, the voltage on the terminal common to the resistors 254 and 256 is ordinarily greater than the voltage from the reference 260. Furthermore, the voltage on the terminal common to the resistors 256 and 258 is ordinarily greater than the voltage on the reference 260. This causes the amplifiers 260 and 262 to produce outputs which indicate that the primary source 250 is still sufficiently high to obtain a proper operation of the drop controller.

As the drop controller is operated, the voltage from the primary source 250 may decrease unless the primary source is recharged. At some time, the battery 250 may become sufficiently run down so that the voltage from the reference 260 exceeds the voltage on the terminal common to the resistors 254 and 256 and the voltage on the terminal common to the resistors 256 and 258. At such time, the voltages from the difference amplifiers 260 and 262 have a polarity and a sufficient magnitude to activate the AND network 264. This causes the indicator 266 to indicate that the voltage from the primary source 250 is insufficient to operate the drop controller properly.

It is possible that the terminal common to the resistors 254 and 256 may indicate a lower voltage than the voltage from the reference 260 at the same time that the terminal common to the resistors 256 and 258 may indicate a voltage higher than the voltage from the reference 260. As will be appreciated, such a situation would indicate that the circuitry in the drop controller may not be operating properly. Under such circumstances, a signal passes through the AND network 270 and activates the alarm 252.

During the operation of the drop controller, the voltage from the secondary source 252 may be periodically tested on an instantaneous basis. This periodic testing is provided by the operation of the timer 274 to close the switches 276 and 278. When the switches 276 and 278 close, the difference amplifier 280 tests the relative voltages from the secondary source 252 and the voltage reference 260. If the voltage from the terminal common to the resistors 282 and 284 should be less than the reference voltage 260, an indication of an inadequate voltage is provided.

The sequence stepper 222 operates to produce a sequence of events, all of which have been described above. This sequence is as follows:

1. The drop controller is first turned on.
2. The stepper motor 64 closes the passage 46.
3. The drop sensor is tested in accordance with the operation of the system shown in FIG. 5.
4. The emergency motor 78 is cycled, initially to open the passage 46 and then to close the passage 46.
5. Tests are performed on the primary and secondary sources 250 and 252 of energy as described in connection with the embodiment shown in FIG. 7.
6. The stepper motor 64 progressively opens the passage 46 until a first drop flows through the passage 46.
7. The system shown in FIG. 4 operates to regulate to a preset value the rate at which the drops flow through the passage 46.

During normal operation of the drop controller, a sequence is initiated when a test switch 300 on the front panel of the drop controller is operated. This sequence is as follows:

1. The stepper motor 64 closes the passage 46.
2. The emergency motor 78 is tested by opening the passage 46 and then closing the passage.
3. The drop sensor 66 is tested by producing a pulse in the light source 88 in accordance with the operation of the system shown in FIG. 6.
4. The primary source 250 of energy is tested.
5. The stepper motor 64 then opens the passage 46 to the position before the initiation of such testing.
6. The operation of the drop controller is resumed.

Although this application has been disclosed and illustrated with reference to particular applications, the principles involved are susceptible of numerous other applications which will be apparent to persons skilled in the art. The invention is, therefore, to be limited only as indicated by the scope of the appended claims.

We claim:

1. In combination for controlling the passage of fluid drops through a drip chamber,
   means for indicating the passage of the fluid drops through the drip chamber,
   means defining the area of passage of the fluid drops through the drip chamber and adjustably positioned to control the size of the passage,
   means for determining the period of time between the passage of each pair of successive fluid drops through the drip chamber,
   means adjustably preset to provide a desired time period between the passage of each pair of successive fluid drops through the drip chamber,
   means for adjusting the position of the passage-defining means to compensate by a particular increment for each determined time period which is greater by a particular amount than the preset time period, and
   means for adjusting the determined time period between the passage of each pair of successive fluid drops through the drip chamber in accordance with the adjustments in the position of the passage-defining means by a particular increment to provide for additional incremental adjustments in the position of the passage-defining means when the period of time between the passage of that pair of successive fluid drops through the drip chamber, after each adjustment of the time period determined for the passage of that pair of successive fluid drops through the drip chamber, still exceeds the preset time period.

2. The combination set forth in claim 1 wherein the means for determining the period of time between the passage of successive fluid drops through the drip chamber includes means for producing a ramp voltage with a slope dependent upon the preset time period between the successive fluid drops, and the means for adjusting the determined time period includes means for changing the ramp voltage by a particular magnitude in accordance with each adjustment in the position of the passage-defining means by the particular increment.

3. The combination set forth in claim 2 wherein the means for adjusting the determined time period includes means for instantaneously decreasing the ramp voltage by a particular magnitude corresponding to the particular increment in the adjustment of the position of the passage-defining means every time that the ramp voltage reaches a particular magnitude in a greater period of time than the preset time period, and
   the means for adjusting the position of the passage-defining means includes means for adjusting the position of the passage-defining means by the particular increment every time that the ramp voltage reaches the particular magnitude in a greater time period than the desired time period.

4. The combination set forth in claim 3, including, means for adjusting the position of the passage-defining means to adjust for differences between the preset time period and the time period determined for the passage of successive fluid drops through the drip chamber every time that the determined time period is less than the preset time period where the position adjustment is through a variable number of increments corresponding to the difference between the determined time period and the preset time period.

5. In combination for controlling the passage of fluid drops through a drip chamber,
   means for indicating the passage of the fluid drops through the drip chamber,
   means adjustably preset to provide a desired period between the passage of pairs of successive fluid drops through the drip chamber,
   means responsive to the signals from the indicating means for determining the periods between the passage of the pairs of successive fluid drops through the drip chamber,
   means adjustably positioned to control the rate of passage of the pairs of the successive fluid drops through the drip chamber,
   means operatively coupled to the control means and the indicating means for producing an adjustment in the positioning of the adjustable means in a direction to decrease the period of time for the passage of the pairs of the successive fluid drops through the drip chamber when the desired period is greater than the determined period, the adjustment in the positioning of the adjustable means being through a number of increments corresponding to the difference between the desired period and the determined period,
   means operatively coupled to the control means and the indicating means for producing adjustments in the positioning of the adjustable means by a particular number of increments in a direction to decrease the period between the passage of the fluid drops through the drip chamber whenever the desired period is less by a particular value than the determined period, and
   means for adjusting the determined period between the passage of each pair of the successive fluid drops through the drip chamber to compensate for each such adjustment in the positioning of the adjustable means by a particular number of increments to provide for additional adjustments, by the particular number of increments, in the position of the passage defining means when the period of time between the passage of that pair of the successive fluid drops through the drip chamber, after each adjustment of the time period determined from the passage of such pair of the successive fluid drops through the drip chamber, still exceeds the preset time period.

6. The combination set forth in claim 5 wherein the determining means includes means for producing a ramp voltage having a magnitude dependent upon the determination of the period between the passage of the successive fluid drops through the drip chamber, the position-adjusting means includes means for producing adjustments in the positioning of the adjustable means by the particular number of increments every time that the ramp voltage reaches a particular value, and the period-adjusting means includes means for adjusting the ramp voltage by a particular number of decrements corresponding to the particular number of increments every time that the position-adjusting means is adjusted by the particular number of increments.

7. The combination set forth in claim 5 wherein the determining means produces a voltage having a magnitude increasing progressively with progressive increases in the time between the determined passage of the successive drops through the drip chamber, the period-adjusting means produces a change in the magnitude of the voltage from the determining means by the particular number of decrements upon each progression in the voltage from the determing means to a particular value, the position-adjusting means produces and adjustment in the positioning of the adjustable means by the particular number of increments in a direction to increase the rate of the passage of the fluid drops through the drip chamber upon each progression in the voltage from the determining means to the particular value, and means are included for producing changes in the position of the position-adjusting means in a direction to decrease the rate of the passage of the fluid drops through the drip chamber upon each progression in the voltage from the determining means to the particular value in a determined time period less than the preset time period.

8. The combination set forth in claim 7 wherein the means for producing the changes in the position of the position-adjusting means in the direction to decrease the rate of passage of the fluid drops provides for an adjustment in such positioning through a number of increments corresponding to the difference between the preset time period and the determined time period when the determined time period is less than the preset time period.

9. In combination for controlling the passage of fluid drops through a drip chamber, a light source disposed to direct light into the drip chamber, light sensor means disposed relative to the light source and the drip chamber to produce signals in accordance with the intensity of the light passing through the drip chamber, output means responsive to the signals from the light sensor means for producing signals representing the passage of the fluid drops through the drip chamber, means for providing for a passage of the fluid drops through the drip chamber at particular periods of time between successive drops, means for measuring the period of time between the passage of each pair of successive drops through the drip chamber, adjustable means defining an adjustable passage through the drip chamber to control the rate of passage of the fluid drops through the drip chamber in accordance with the adjustments in such adjustable means, stepper means operably coupled to the adjustable means for incrementally adjusting the position of the adjustable means to open and close the passage through the drip chamber, means responsive to each measured period less than the particular period for obtaining an operation of the stepper means, through a number of increments representative of the difference between the measured period and the particular period, in a direction for decreasing the rate at which the fluid drops pass through the drip chamber, means responsive to each measured period greater by a particular value than the particular period for obtaining an operation of the stepper motor through a particular number of increments in a direction for increasing the rate at which each pair of the successive fluid drops pass through the drip chamber where the particular number of increments may be less than that required to make the measured period equal to the particular period, and means responsive to each stepping of the stepping means through the particular number of increments for decreasing the measured period of time between the passage of each pair of successive drops through the drip chamber in accordance with such particular number of increments to provide for additional incremental adjustments in the position of the adjustable means when the period of time between such pair of successive drops again exceeds the particular period.

10. The combination set forth in claim 9 wherein the means operating the stepper means in a direction to increase the rate of passage of the fluid drops through the drip chamber includes:

means for producing a voltage representative of the period of time between the passage of successive drops through the drip chamber, means for providing a particular voltage, and means for comparing the representative voltage with the particular voltage to obtain the operation of the stepper means through the particular number of increments when the representative voltage exceeds the particular voltage and wherein the means operating the stepper means in a direction to decrease the rate of passage of the fluid drops through the drip chamber operates instantaneously to decrease such rate by a number of increments representative of the difference between the measured period and the particular period when the particular period is greater than the measured period.

11. The combination set forth in claim 10 wherein the means operating the stepper means in the direction to increase the rate of fluid drops includes:

means for decreasing the representative voltage by a particular value, for each period between the passage of a pair of successive drops of fluid through the drip chamber, in accordance with each incremental stepping of the stepper means through the particular number of increments until the representative voltage for the passage of that pair of successive drops of fluid through the drip chamber is substantially equal to the particular voltage upon the passage of the next drop in that pair through the drip chamber.

12. The combination set forth in claim 9 wherein the means operating the stepper means in the direction to increase the rate of passage of the fluid drops incrementally decreases the measured time period between the times for the passage of such pair of successive drops through the drip chamber, upon each incremental stepping of the stepping means through the particular number of increments, until the measured time period between the time for the passage of such pair of successive drops through the drip chamber corresponds to the particular time period.

13. The combination set forth in claim 12 wherein the adjustable means includes a housing and a resilient diaphragm disposed in the housing and cooperating with the housing deformable to define the passage and further includes a rod disposed against the diaphragm and operative by the stepper means to deform the diaphragm relative to the housing for adjusting the passage.

14. In combination for controlling the passage of fluid drops through a drip chamber having an adjustable passage, a source disposed to direct energy into the drip chamber, sensor means disposed relative to the source and the drip chamber to produce signals in accordance with the intensity of the energy passing through the drip chamber from the source, output means responsive to the signals from the sensor means for producing signals representing the passage of the fluid drops through the drip chamber, control means adjustably preset to provide a desired rate for the passage of the fluid drops through the drip chamber, means responsive to the signals from the output means for indicating the actual rate for the passage of the fluid drops through the drip chamber, means for providing an adjustable passage in the drip chamber, means adjustable in position for adjusting the adjustable passage in the drip chamber in accordance with such adjustments in position to control the rate at which the fluid drops pass through the drip chamber, means operatively coupled to the adjustable means and the indicating means for producing an instantaneous adjustment in the positioning of the adjustable means in a direction to decrease the rate of passage of the fluid drops through the drip chamber by an amount representative of the difference between the desired and actual rates when the desired rate is less than the actual rate, means operatively coupled to the control means and the indicating means for producing predetermined incremental adjustments in the positioning of the adjustable means in a direction to increase the rate of passage of the fluid drops through the drip chamber when the desired rate becomes greater than the actual rate during the measurement of the time period between the passage of each pair of successive fluid drops through the drip chamber, and means responsive to each predetermined incremental adjustment in the positioning of the adjustable means for instantaneously adjusting the indication of the actual rate of the passage of each pair of successive fluid drops through the drip chamber to a value below the desired rate in accordance with such predetermined incremental adjustments to obtain additional incremental adjustments when the actual rate of the passage of such pair of successive fluid drops becomes greater than the desired rate.

15. The combination set forth in claim 14, including, means for regulating the energy from the source at a particular value.

16. The combination set forth in claim 14, including, means for instantaneously decreasing the energy from the source to obtain the production by the sensor means of a signal simulating the sensing of a drop by the sensor means, and means operatively coupled to the sensor means for indicating whether the sensor means is providing an indication of a simulated drop when the energy from the source is instantaneously decreased by the previously recited means.

17. The combination set forth in claim 14, including, means for determining whether the rate of flow of the fluid is within correctable limits when the actual rate of flow is below the desired rate, and means for closing the drip chamber when the actual rate is below the desired rate by an amount which is not within correctable limits.

18. The combination set forth in claim 14, including, means responsive to each incremental adjustment in the positioning of the adjustable means for the passage of each pair of successive drops of fluid through the drip chamber for producing a decrease in the actual rate indicated by the indicating means for the pasage of that pair of successive drops of fluid through the drip chamber to provide for a new comparison of the rates from the control means and the indicating means for that pair of successive drops of fluid through the drip chamber.

19. In combination for controlling the rate of flow of drops of fluid through a drip chamber, means for introducing energy to the drip chamber, means for sensing the energy passing from the drip chamber and for producing signals representing the sensed energy, valve means associated with the drip chamber and adjustable to define the opening through the drip chamber for the passage of the fluid drops, a stepper motor for operating the valve means, means for initially operating the stepper motor in a direction for obtaining a closure of the drip chamber, means operatively coupled to the sensing means for testing the operability of the sensor means, an emergency motor for operating the valve means, means operatively coupled to the emergency motor for cycling the emergency motor between the open and closed positions of the valve means and for discontinuing the operation of the emergency motor when the valve means is in the closed position, means for sensing the operation of the emergency motor to insure the movement of the valve means between the open and closed positions of the valve means and the discontinuance in the operation of the emergency motor when the valve means is in the closed position, means for operating the stepper motor, after the movement of the valve means to the closed position by the emergency motor, to open the valve means until the initiation of the passage of a first fluid drop through the drip chamber, and servo means responsive to the initiation of the passage of fluid drops through the drip chamber for operating the stepper motor to maintain the rate of the passage of the drops of fluid through the chamber at a particular value.

20. The combination set forth in claim 19 wherein the servo means includes:

first means responsive to the signals from the sensing means for indicating the time between the passage of each pair of successive drops through the drip chamber, second means responsive to the failure of the first means to indicate the passage of each pair of successive drops through the drip chamber within a time corresponding to the particular rate for operating the stepper motor to obtain an incremental opening of the valve means, and third means responsive to the operation of the stepper motor, upon the failure of the first means to indicate the passage of each pair of successive drops through the drip chamber within the time limit corresponding to the particular rate, for decreasing the indicated time between the passage of that pair of successive drops through the drip chamber by an amount related to each incremental operation of the stepper motor to provide for additional incremental adjustments in the position of the passage-defining means for that pair of successive fluid drops through the drip chamber when the indicated time between the passage of that pair of successive drops through the drip chamber again becomes greater than the time corresponding to the particular rate, and the servo means further includes:

fourth means responsive to the signals from the sensing means for operating the stepper motor to provide instantaneous decreases in the rate of passage of the fluid drops through the drip chamber, when the time between the passage of successive drops through the drip chamber is less than the time corresponding to the particular rate, through a number of increments representative of the difference in time between the time corresponding to the particular rate and the time between the passage of successive drops through the drip chamber.

21. The combination set forth in claim 20, including, the servo means including data processing means, operative to process data at a particular rate, for processing the data representing the rate of the passage of each pair of the successive fluid drops through the drip chamber to control the operation of the stepper motor in maintaining the rate of the passage of such pair of the successive drops of fluid through the drip chamber at the particular value, means for checking the rate at which the data processing means processes the data representing the rate of the passage of the fluid drops through the drip chamber, and means responsive to the rates, below the particular rate, in the operation of the data processing means in processing data for operating the emergency motor to close the valve means.

22. The combination set forth in claim 19 wherein the testing means for the sensor means includes:

means for providing for a decrease in the energy introduced to the drip chamber and means responsive to the energy from the sensor means for determining if the sensor means produces a signal, corresponding to that representative of the passage of a fluid drop through the drip chamber, upon the decrease in the energy introduced to the drip chamber in accordance with the operation of the previously recited means, and wherein means are included for operating a particular one of the stepper motor and the emergency motor in a direction to close the valve means when the determining means fails to indicate the production by the sensor means of a signal corresponding to that representative of the passage of a fluid drop through the drip chamber.

23. The combination set forth in claim 19, including, means for inhibiting any effects of splash-up of fluid drops passing through the drip chamber in determining the rate of passage of the fluid drops through the drip chamber.

24. In combination for controlling the rate of passage of fluid drops through a drip chamber, a stepper motor, valve means adjustable to control the rate of passage of fluid drops through the drip chamber, the valve means being coupled to the stepper motor to be operated by the stepper motor to provide such adjustments in the valve means, means for determining the rate at which the fluid drops pass through the drip chamber, means for pre-setting a particular value for the rate of passage of the fluid drops through the drip chamber, means for initially operating the stepper motor in a direction to obtain a closure of the drip chamber to the passage of the fluid drops through the drip chamber, means for subsequently operating the stepper motor progressively in a direction to open the drip chamber until the initiation of the passage of fluid drops through the drip chamber, and means responsive to the initiation of the passage of the fluid drops through the drip chamber for subsequently regulating the rate of passage of the fluid drops through the drip chamber to the particular value, the regulating means including:

means for providing for incremental changes of predetermined value at progressive instants of time in the rate of passage of each pair of successive drops of the fluid through the drip chamber for rates below the particular value, means responsive to each incremental change in the predetermined value in the rate of passage of each pair of successive drops of the fluid through the drip chamber for producing an increase in the rate determined for the passage of that pair of the successive drops of the fluid through the drip chamber until the production of rates at the particular valve for the passage of that pair of the successive drops of the fluid through the drip chamber, and means for providing for analog changes in the rate of passage of the fluid drops through the drip chamber for rates above the particular value where such analog changes correspond instantaneously to the difference between the determined rate and the particular rate.

25. The combination set forth in claim 24, including, means for producing an alarm when the valve means is not able to be operated to open the drip chamber by an amount respresentative of the difference between the particular value and the determined rate at which the pairs of successive drops of the fluid are passing through the drip chamber.

26. The combination set forth in claim 24, including, means for sensing the disposition of the valve means in the open and closed positions of the drip chamber, and
means operatively coupled to the sensing means for initially adjusting the valve means on a cyclic basis between the open and closed positions of the drip chamber before the initiation of the passage of the fluid drops through the drip chamber and for then terminating the movement of the valve means at the closed position before the passage of the fluid drops through the drip chamber.

27. The combination set forth in claim 24, including, means responsive to the regulation of the rate of passage of the fluid drops through the drip chamber at a zero rate for producing an alarm.

28. The combination set forth in claim 24, including, an emergency motor, and
means for operatively coupling the emergency motor to the adjusting means for obtaining a cyclic operation of the emergency motor in adjusting the valve means between the open and closed positions of the drip chamber and then, before the operation of the stepper motor to initiate the passage of the fluid drops through the drip chamber, terminating the operation of the emergency motor at the close position of the valve means.

29. The combination set forth in claim 24, including, an emergency motor,
means for initially stepping the stepper motor to the position corresponding to the closed position of the drip chamber before the initiation of the passage of fluid flow through the drip chamber,
means for coupling the emergency motor to the valve means, after the closure of the drip chamber by the stepper motor, and for operating the emergency motor after such coupling to cycle the valve means between the closed and open positions of the drip chamber and for terminating the operation of the emergency motor at the closed position of the drip chamber, and
means for testing for the adjustment of the valve means by the emergency motor between the closed and open positions of the drip chamber.

30. The combination set forth in claim 24, including, the regulating means including:
means for introducing the light to the drip chamber,
means for sensing the light passing from the drip sensor,
means for instantaneously decreasing the intensity of the light introduced to the drip chamber, and
means for determining any decrease in the light sensed by the sensing means upon the instantaneous decrease in the intensity of the light introduced to the drip chamber.

31. The combination set forth in claim 24, including, the rate-determining means including means for introducing energy to the drip chamber and means for sensing the energy passing from the drip chamber,
means for maintaining at a particular value the intensity of the energy introduced to the drip chamber during the passage of the fluid drops through the drip chamber, and
means for inhibiting the effects on the sensing means of splash-up of fluid drops passing through the drip chamber.

32. The combination set forth in claim 24, including, an emergency battery, and
means for testing the operability of the emergency battery before the initiation of the passage of the fluid drops through the drip chamber.

33. The combination set forth in claim 24, including, a primary source of electrical energy for providing for the passage of the fluid drops through the drip chamber,
a voltage dividing network connected to the primary energy source, and
means connected to the voltage dividing network for indicating if the energy from the primary source is at least equal to a particular level.

34. The combination set forth in claim 24, including, an alarm, and
means responsive to a setting of the valve means to the open position and to an the particular value being greater than the actual rate for obtaining an operation of the alarm.

* * * * *